(12) United States Patent
Zimmermann

(10) Patent No.: US 6,292,537 B1
(45) Date of Patent: Sep. 18, 2001

(54) X-RAY DIAGNOSTIC DEVICE INCLUDING MEANS FOR DETERMINING THE DOSE

(75) Inventor: Robert Zimmermann, Hamburg (DE)

(73) Assignee: U.S. Philips Corporation, New York, NY (US)

( * ) Notice: Subject to any disclaimer, the term of this patent is extended or adjusted under 35 U.S.C. 154(b) by 0 days.

(21) Appl. No.: 09/493,963

(22) Filed: Jan. 28, 2000

(30) Foreign Application Priority Data

Jan. 30, 1999 (DE) .................................... 199 03 749

(51) Int. Cl.[7] ........................................ H05G 1/44
(52) U.S. Cl. ............................... 378/108; 378/97
(58) Field of Search ...................... 378/97, 108, 207

(56) References Cited

U.S. PATENT DOCUMENTS 5,625,662 * 4/1997 Toth et al. ......................... 378/16

FOREIGN PATENT DOCUMENTS 2124035    11/1972 (DE) ................................ H05G/1/26

* cited by examiner

Primary Examiner—Robert H. Kim
Assistant Examiner—Jurie Yun
(74) Attorney, Agent, or Firm—John F. Vodopia

(57) ABSTRACT

The invention relates to an X-ray diagnostic device in which the dose applied to a patient is determined and in which the effective dose which is of relevance for the radiation load is calculated from this dose as well as from a weighting factor which is fetched in dependence on the relevant anatomical region to be examined.

3 Claims, 1 Drawing Sheet

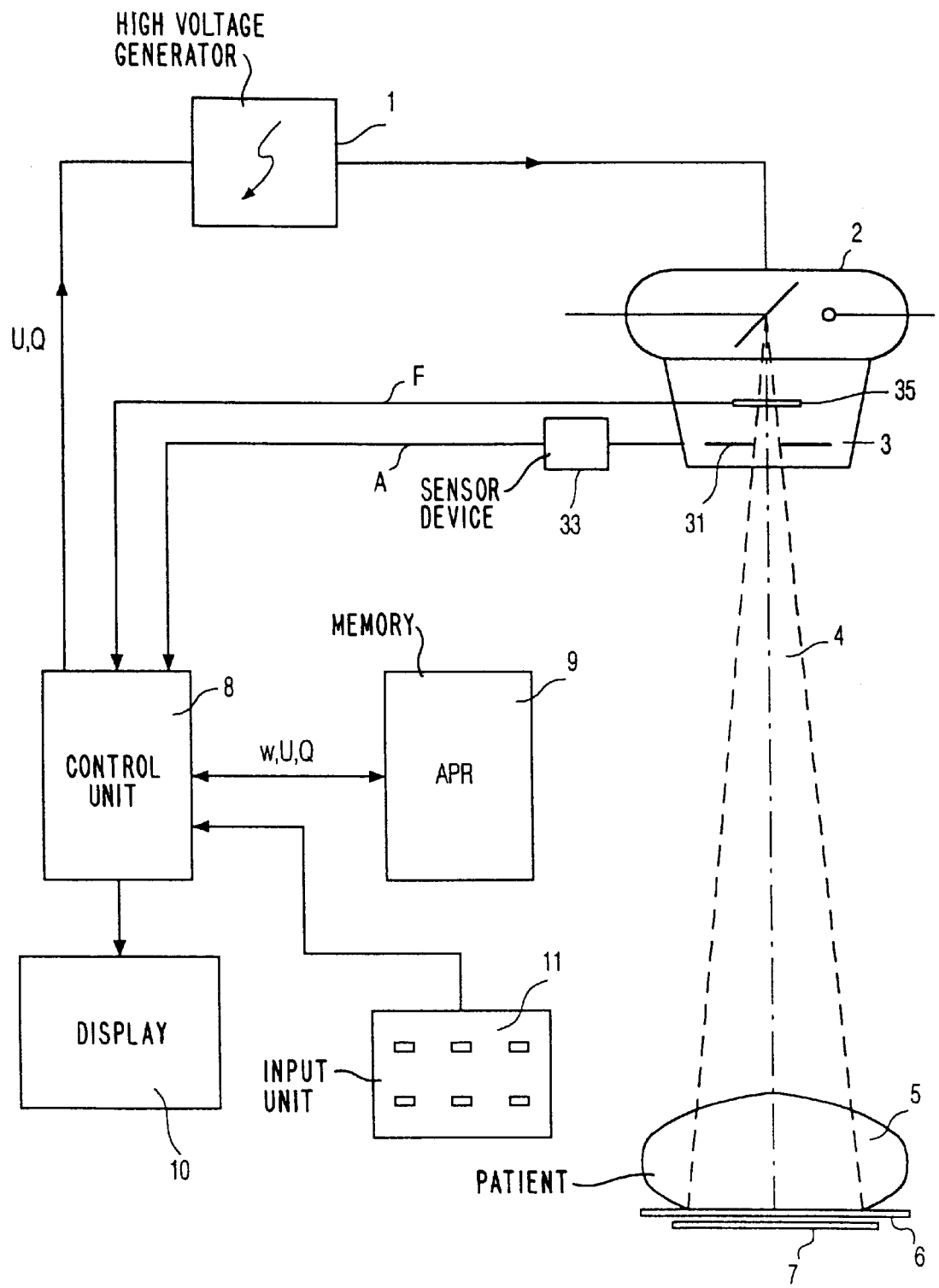

X-RAY DIAGNOSTIC DEVICE INCLUDING MEANS FOR DETERMINING THE DOSE

BACKGROUND OF THE INVENTION

1. Field of the Invention

The invention relates to an X-ray diagnostic device which includes an X-ray generator for feeding an X-ray source and means for determining the dose applied during an X-ray examination of a patient.

2. Description of Related Art

An X-ray diagnostic device of this kind is known from DE-OS 2 124 035 (page 2, second paragraph). The dose is measured therein by means of an ionization chamber which is attached to an ionization chamber connected to the X-ray source. The ionization chamber has such a large surface area that it intercepts all X-rays emanating from the primary diaphragm even in the case of the maximum radiation field size that can be adjusted by means of the primary diaphragm. The output signal of the ionization chamber thus corresponds to the dose surface product measured in $\mu Gy*m^2$.

The dose surface product is a purely physical quantity which corresponds to the surface integral of KERMA (Kinetic Energy Released in MAtter) in air. This physical quantity only conditionally provides information about the radiation load for the patient being examined or about the effective dose which takes into account the various risks of the individual organs or tissues in respect of stochastic irradiation. When exposed to the same applied dose surface product, for example, the X-rays will damage the bladder of a patient significantly more than the skull of the patient.

Citation of a reference herein, or throughout this specification, is not to be construed as an admission that such reference is prior art to the Applicant's invention of the invention subsequently claimed.

SUMMARY OF THE INVENTION

Therefore, it is an object of the invention to construct an X-ray diagnostic device of the kind set forth in such a manner that the radiation load for a patient can be more accurately indicated during an X-ray examination. This object is achieved according to the invention in that there is provided a storage device in which a respective set of exposure and/or fluoroscopy parameters is stored for a number of organs, that each set includes, in addition to exposure or fluoroscopy parameters for the X-ray generator, a weighting factor which corresponds to the biological effect of the radiation on the relevant organ, and that there is provided an arithmetic unit for calculating the effective dose from the dose and the weighting factor.

A memory in which a respective set of exposure or fluoroscopy parameters is stored for a number of organs is customarily used in contemporary X-ray generators and is referred to as APR (Anatomically Programmed Radiography). For an X-ray exposure, the user enters the organ to be examined or the anatomical region (for example "lung p.a."), the optimum exposure parameters (inter alia the voltage applied to the X-ray source) for an X-ray exposure of this organ then being fetched from the memory so as to be automatically adjusted.

The invention is based on the recognition of the fact that to each organ there can be assigned a weighting factor which is a measure of the biological effect of the dose during an X-ray examination of the relevant organ. The effective dose which is a measure of the biological effect of the X-rays in the patient can be calculated by multiplying said weighting factor by the dose determined during the X-ray examination (i.e. the KERMA in air).

The invention can be used not only for X-ray apparatus in which only X-ray images can be formed, such as the so-called Bucky devices, but also in X-ray apparatus with an exposure mode as well as a fluoroscopy mode. In contemporary apparatus of this kind the fluoroscopy parameters for different organs or anatomical regions can also be stored; in the case of a change-over to the X-ray exposure mode, the exposure parameters are then either derived from the fluoroscopy parameters or fetched from a separate memory containing the exposure parameters for the relevant organ.

The dose, or the dose surface product, can be measured by means of a suitable measuring chamber. The further embodiment additionally comprising means for measuring the geometrical parameters of the X-ray examination and means for calculating the dose from the geometrical parameters and the exposure or fluoroscopy parameters does not require such a measuring chamber; the dose is derived on the one hand from the exposure or fluoroscopy parameters (voltage applied to the X-ray source or the time integral of the current through the X-ray source, filtering etc.) and on the other hand from geometrical parameters of the X-ray examination (for example, the aperture of the X-ray beam).

A preferred embodiment of the means for measuring the geometrical parameters includes a measuring device for measuring the aperture of a primary beam diaphragm connected to the X-ray source.

BRIEF DESCRIPTION OF THE DRAWING

The invention will be described in detail hereinafter with reference to a drawing which is a purely diagrammatic representation of an X-ray device according to the invention.

DETAILED DESCRIPTION OF THE PREFERRED EMBODIMENT

An X-ray generator 1 supplies the high voltage for an X-ray source 2 as well as the current through the X-ray source. A primary beam diaphragm 3 is connected to the X-ray source 2 and includes a first collimator pair 31 with collimator edges which extend perpendicularly to the plane of drawing and define the aperture in the plane of drawing of the radiation beam 4 emitted by the X-ray source. A second collimator pair (not shown) with collimator edges extending parallel to the plane of drawing defines the aperture of the radiation beam 4 in the direction perpendicular to the plane of drawing. The radiation beam 4 traverses a patient 5 accommodated on a patient table 6. The X-ray image produced by the irradiation is picked up by a suitable image converter 7.

The high voltage for and the current through the, X-ray source 2, produced by the X-ray generator, and the temporal variation of these quantities are preselected by a control unit 8, for example a microprocessor which co-operates with a memory 9. The control unit 8 is coupled to a display unit or monitor 10 and also to an input unit 11 (keyboard, mouse or trackball) via which a user can predetermine the execution of the subsequent X-ray examination and whereby the user can notably select the organ or anatomical region to be examined during a subsequent X-ray exposure.

The effective dose $D_{eff}$ is calculated as:

$$D_{eff} = c \cdot \gamma \cdot Q \cdot A \cdot w$$

Therein, c is a constant and $\gamma$ is a factor which is dependent on the high voltage U across the X-ray tube as well as on the filter 35 which is active in the beam path and incorporated in the primary diaphragm 3. Q corresponds to the time integral of the current through the X-ray tube (generally speaking, this is the tube current multiplied by the duration of an X-ray exposure), and A represents the aperture of the radiation beam or the cross-sectional area of the radiation beam limited by the collimator pair 31. The product $c \cdot \gamma \cdot Q \cdot A$ corresponds to the dose D. w is a weighting factor which describes the biological effect of the X-rays in the relevant anatomical region being examined.

For an X-ray exposure the examiner selects the region to be examined, for example "lung p.a." via the input unit 11. The control unit 8 then fetches the exposure parameters, stored in the storage device 9, for optimum exposure of this region, that is to say the tube voltage U, the mAs product, corresponding to the factor Q, as well as a weighting factor w associated with the relevant anatomical region. On the, basis of the tube voltage thus fetched and the filtering taking place in the beam path, conveyed to the control unit 8 by the signal F, the control unit then calculates the factor $\gamma$. The cross-sectional area A of the radiation beam is provided by a sensor device 33 which may include, for example potentiometers which are coupled to the collimator pairs in the primary beam diaphragm. The control unit 8 can determine the effective dose for the exposures of the anatomical region from the selected parameters or the parameters determined in the control unit 8.

The effective dose $D_{eff}$ can be determined analogously during X-ray fluoroscopy; the weighting factor w and the tube voltage U are then fetched from the storage device 9 in dependence on the selected anatomical region. The control unit then forms the quantity Q by forming the time integral over the tube current flowing through the X-ray tube during fluoroscopy.

When the collimator pairs 31 are opened wide, parts of other organs for which the X-rays have a different biological effect could also be present in the beam path. This may mean that in the case of an exposure with a large radiation field a weighting factor must be used other than that used in the case of an exposure with a small radiation field. This can be realized by making the weighting factor w also dependent on the cross-sectional area A of the collimator device. The foregoing can be achieved, for example by storing a plurality of weighting factors in the storage device 9 for one anatomical region, one of said weighting factors being selected in dependence on the relevant value A in order to calculate the effective dose on the basis thereof.

As has already been described, the dose D can be determined by measurement instead of calculation. The effective dose is then obtained by multiplication of the measured value by a weighting factor w.

All references cited herein, as well as the priority document German Patent Application 19903749.3 filed Jan. 30, 1999, are incorporated herein by reference in their entirety and for all purposes to the same extent as if each individual publication or patent or patent application was specifically and individually indicated to be incorporated by reference in its entirety for all purposes.

What is claimed is:

1. An X-ray diagnostic device comprising:

an X-ray source, an X-ray generator for feeding the X-ray source, a storage device in which a respective set of exposure and/or fluoroscopy parameters is stored for a number of organs, wherein each set includes exposure or fluoroscopy parameters for the X-ray generator, and a weighting factor which corresponds to the biological effect of the radiation on the relevant organ, and means for determining the dose applied during an X-ray examination of a patient which includes an arithmetic unit for calculating the effective dose from the dose and the weighting factor.

2. An X-ray diagnostic device as claimed in claim 1 further comprising means for measuring the geometrical parameters of the X-ray examination, and means for calculating the dose from the geometrical parameters and the exposure or fluoroscopy parameters.

3. An X-ray diagnostic device as claimed in claim 1 wherein the means for measuring the geometrical parameters include a measuring device for measuring the aperture of a primary beam diaphragm connected to the X-ray source.

* * * * *